US009784703B2

(12) United States Patent
Budde (10) Patent No.: US 9,784,703 B2
(45) Date of Patent: Oct. 10, 2017

(54) METHOD FOR AIR FLOW FAULT AND CAUSE IDENTIFICATION

(71) Applicant: SCHNEIDER ELECTRIC IT CORPORATION, West Kingston, RI (US)

(72) Inventor: Kristian Budde, Kolding (DK)

(73) Assignee: SCHNEIDER ELECTRIC IT CORPORATION, West Kingston, RI (US)

( * ) Notice: Subject to any disclaimer, the term of this patent is extended or adjusted under 35 U.S.C. 154(b) by 301 days.

(21) Appl. No.: 14/655,553

(22) PCT Filed: Dec. 28, 2012

(86) PCT No.: PCT/US2012/071910
§ 371 (c)(1),
(2) Date: Jun. 25, 2015

(87) PCT Pub. No.: WO2014/105031
PCT Pub. Date: Jul. 3, 2014

(65) Prior Publication Data
US 2015/0330924 A1    Nov. 19, 2015

(51) Int. Cl.
*G01N 25/72* (2006.01)
*G01F 1/00* (2006.01)
(Continued)

(52) U.S. Cl.
CPC ........... *G01N 25/72* (2013.01); *F24F 11/022* (2013.01); *G01F 1/00* (2013.01); *G01K 3/005* (2013.01);
(Continued)

(58) Field of Classification Search
CPC .. G01K 7/02; G01K 7/10; G01K 7/22; G01K 11/32; G01K 13/00; G01K 13/02; G01K 2205/04; G01K 2013/024; G01K 3/005; G01K 3/10; G01K 7/42; G01J 5/004; G01J 5/043; G01J 5/0821; H01R 4/023;
(Continued)

(56) References Cited

U.S. PATENT DOCUMENTS 5,582,021 A * 12/1996 Masauji ............. B60H 1/00978
236/91 R
5,612,677 A    3/1997 Baudry
(Continued)

OTHER PUBLICATIONS

Notification of Transmittal of the International Search Report and the Written Opinion of the International Searching Authority from corresponding PCT/US2012/071910 dated Feb. 22, 2013.
(Continued)

*Primary Examiner* — Manish S Shah
(74) *Attorney, Agent, or Firm* — Lando & Anastasi, LLP (57) ABSTRACT

Methods and systems for detecting and identifying faults in air-cooled systems are provided. The systems and methods may utilize a prediction model based on an energy balance relationship. In certain methods, one or more measured parameters associated with the air-cooled system may be compared with corresponding parameters generated by the prediction model. One or more faults may be detected and identified based upon deviations between the measured and detected system parameters.

20 Claims, 4 Drawing Sheets

(51) Int. Cl.
| | |
|---|---|
| *F24F 11/02* | (2006.01) |
| *G01K 7/42* | (2006.01) |
| *H05K 7/20* | (2006.01) |
| *G01K 3/00* | (2006.01) |
| *G01K 3/10* | (2006.01) |
| *F24F 11/00* | (2006.01) |

(52) U.S. Cl.
CPC .............. *G01K 3/10* (2013.01); *G01K 7/42* (2013.01); *H05K 7/20945* (2013.01); *F24F 11/0012* (2013.01); *F24F 2011/0052* (2013.01); *F24F 2011/0093* (2013.01)

(58) Field of Classification Search
CPC ........ H01R 4/029; H01R 43/28; B23K 31/02; H01C 7/008; H01C 17/00; G01F 1/00; G01N 25/72; G01N 33/02; H05K 7/20945; F24F 11/0012; F24F 2001/0052; F24F 2011/0093; F24F 11/022; H02M 1/32; H02M 1/38; H02M 1/53806; G01R 31/2642; G01R 31/048; G01R 31/40; A47J 43/287; F16B 2/02; F16B 1/00; F16B 47/00; F16B 2001/0035; F16M 13/02; F16M 13/022
See application file for complete search history.

(56) References Cited

U.S. PATENT DOCUMENTS

| | | | |
|---|---|---|---|
| 6,223,544 B1 | 5/2001 | Seem | |
| 6,225,141 B1* | 5/2001 | Wenner | G01K 15/00 374/E15.001 |
| 6,658,373 B2* | 12/2003 | Rossi | F24F 11/0086 702/183 |
| 6,758,265 B2* | 7/2004 | Henry | G05D 23/1934 454/75 |
| 6,981,383 B2* | 1/2006 | Shah | F24F 3/0442 236/18 |
| 2005/0251364 A1 | 11/2005 | Kang et al. | |
| 2008/0183424 A1 | 7/2008 | Seem | |
| 2009/0190625 A1 | 7/2009 | Chung et al. | |
| 2011/0071687 A1 | 3/2011 | Uraki et al. | |
| 2011/0093424 A1 | 4/2011 | Zimmermann et al. | |
| 2012/0052785 A1 | 3/2012 | Nagamatsu et al. | |
| 2013/0060385 A1* | 3/2013 | Leen | F24F 11/0009 700/276 |

OTHER PUBLICATIONS

Extended European Search Report from corresponding European Application No. 12891200.3 dated Jun. 28, 2016.

* cited by examiner

# METHOD FOR AIR FLOW FAULT AND CAUSE IDENTIFICATION

This application is a U.S. National Stage Application under 35 U.S.C. §371 from International Application No. PCT/US2012/071910, filed Dec. 28, 2012, which is hereby incorporated by reference in its entirety for all purposes.

FIELD OF THE DISCLOSURE

This disclosure relates to air-cooled systems, and particularly to methods and systems directed toward identifying faults in air-cooled systems.

BACKGROUND OF THE DISCLOSURE

Air-cooled power modules, such as power inverters, rely on a sufficient flow of air to remove heat generated during normal modes of operation. The capacity to provide adequate cooling in an air-cooled system may be compromised by faults related to one or more causes. For example, an air filter may become clogged from a dusty environment or from inadequate maintenance procedures. Heat sinks associated with a particular power module may also become clogged or otherwise compromised due to missing or leaking air filters. In addition, physical objects may block the flow of air, for example, when a power module not designed for wall-mounting is physically installed on a wall. Air-cooling may be provided by one or more fans, and the fans themselves may fail or otherwise be incapable of supplying a sufficient flow of air. For example, the fan motor may malfunction, or the fan may be placed in an environment where there is an inadequate supply of air.

In some instances, inadequate cooling may trigger a safety measure that causes the power module to be powered down. It would therefore be advantageous to detect and identify a fault associated with inadequate cooling before resorting to shutting down the module. In addition, the ability to determine if sufficient cooling is available and to identify one or more causes of faults related to air flow would be helpful in creating an autonomous system that has the ability to quickly detect and self-diagnose different sources of faults. Detecting and identifying the cause of a fault related to airflow may allow a field service engineer to quickly respond and resolve the problem based on the specific type of fault. This would decrease downtime in one or more systems, and subsequently increase overall efficiency.

SUMMARY OF THE DISCLOSURE

By way of introduction, aspects of the disclosure provide a method of identifying faults in an air-cooled system. The air-cooled system may include a first temperature sensor configured to detect a temperature of an exhaust heat, a second temperature sensor configured to detect a temperature of a heat sink, and an air flow sensor configured to detect a rate of air flow through an air-cooling device. The method may include measuring a first series of temperatures with the first temperature sensor to produce a first time series of first measured temperature values. In some aspects, the method may further include measuring a second series of temperatures with the second temperature sensor to produce a second time series of second measured temperature values. In at least one aspect, the method may further include measuring a series of rates of air flow with the air flow sensor to produce a time series of measured air flow rate values. In various aspects, the method may further include identifying a fault in response to at least one of: the first time series of the first measured temperature values being outside an acceptable range of a first target value, the second time series of the second measured temperature values being outside an acceptable range of a second target value, and the time series of the measured air flow rate values being outside an acceptable range of a third target value.

According to one or more aspects, identifying the fault may include calculating a difference between consecutive measured values in the first time series to produce a first series of consecutive difference values related to the first measured temperature. In another aspect, identifying the fault may include calculating a difference between consecutive measured values in the second time series to produce a second series of consecutive difference values related to the second measured temperature. In yet another aspect, identifying the fault may include calculating a difference between consecutive measured values in the time series of the measured air flow rate to produce a series of consecutive difference values related to the measured air flow rate.

In certain embodiments, the method may include determining a first type of fault based upon: the first series of consecutive difference values related to the first measured temperature are above the acceptable range of the first target value, the second series of consecutive difference values related to the second measured temperature are above the acceptable range of the second target value, and the series of consecutive difference values related to the measured air flow rate are within the acceptable range of the third target value.

According to another embodiment, the method may include determining a second type of fault based upon: the first series of consecutive difference values related to the first measured temperature are within the acceptable range of the first target value, the second series of consecutive difference values related to the second measured temperature are above the acceptable range of the second target value, and the series of consecutive difference values related to the measured air flow rate are within the acceptable range of the third target value.

In at least one embodiment, the method may include determining a third type of fault based upon: the first series of consecutive difference values related to the first measured temperature are above the acceptable range of the first target value, the second series of consecutive difference values related to the second measured temperature are above the acceptable range of the second target value, and the series of consecutive difference values related to the measured air flow rate are below the acceptable range of the third target value.

In certain embodiments, the method may include determining a fourth type of fault based upon: at least one consecutive difference value related to the measured air flow rate is below the acceptable range of the third target value.

According to certain embodiments, the air-cooled system may further include a third temperature sensor configured to detect a temperature of ambient air. In at least one aspect, the method may include measuring a third series of temperatures with the third temperature sensor to produce a third time series of third measured temperature values.

In various aspects, the first target value may be created by calculating a predicted exhaust heat temperature. In another aspect, the second target value may be created by calculating a predicted heat sink temperature. In at least one aspect, the predicted exhaust heat temperature and predicted heat sink temperature may be calculated by a prediction model. In some embodiments, the prediction model may be configured to generate the predicted exhaust heat temperature and predicted heat sink temperature based upon the time series of measured air flow rate values, the third time series of third measured temperature values, a system load value, and design parameters of the air-cooled system. In various embodiments, the prediction model may be based upon an energy balance relationship according to the equation: $Q=cm\Delta T$.

In accordance with one or more embodiments, a detection system for identifying faults in an air-cooled system is provided. In certain embodiments, the air-cooled system may be of the type used to cool air-cooled equipment. According to various aspects, the air-cooled system may include a heat sink. In various embodiments, the detection system may include an air-cooling device configured to direct air over the heat sink. In certain embodiments, the detection system may include a first temperature sensor configured to detect a temperature of an exhaust heat associated with the air-cooled equipment. In another embodiment, the detection system may include a second temperature sensor configured to detect a temperature of the heat sink. In yet another embodiment, the detection system may include an air flow sensor configured to detect a rate of air flow through the air-cooling device. In various aspects, the detection system may include a controller in communication with the first temperature sensor, the second temperature sensor, and the air flow sensor. According to at least one aspect, the controller may be configured to measure a first series of temperatures with the first temperature sensor to produce a first time series of first measured temperature values. In a further aspect, the controller may be configured to measure a second series of temperatures with the second temperature sensor to produce a second time series of second measured temperature values. In some aspects, the controller may be configured to measure a series of rates of air flow with the air flow sensor to produce a time series of measured air flow rate values. According to various aspects, the controller may be configured to identify a fault in response to at least one of: the first time series of the first measured temperature values being outside an acceptable range of a first target value, the second time series of the second measured temperature values being outside an acceptable range of a second target value, and the time series of the measured air flow rate values being outside an acceptable range of a third target value.

In accordance with at least one embodiment, the controller may be configured to identify the fault by calculating a difference between consecutive measured values in the first time series to produce a first series of consecutive difference values related to the first measured temperature, calculating a difference between consecutive measured values in the second time series to produce a second series of consecutive difference values related to the second measured temperature, and calculating a difference between consecutive values in the time series of the measured air flow rate values to produce a series of consecutive difference values related to the measured air flow rate.

According to a further aspect, the controller may be configured to determine a first type of fault based upon: the first series of consecutive difference values related to the first measured temperature are above the acceptable range of the first target value, the second series of consecutive difference values related to the second measured temperature are above the acceptable range of the second target value, and the series of consecutive difference values related to the measured air flow rate are within the acceptable range of the third target value.

According to another aspect, the controller may be configured to determine a second type of fault based upon: the first series of consecutive difference values related to the first measured temperature are within the acceptable range of the first target value, the second series of consecutive difference values related to the second measured temperature are above the acceptable range of the second target value, and the series of consecutive difference values related to the measured air flow rate are within the acceptable range of the third target value.

In at least one aspect, the controller may be configured to determine a third type of fault based upon: the first series of consecutive difference values related to the first measured temperature are above the acceptable range of the first target value, the second series of consecutive difference values related to the second measured temperature are above the acceptable range of the second target value, and the series of consecutive difference values related to the measured air flow rate are below the acceptable range of the third target value.

In a further aspect, the controller may be configured to determine a fourth type of fault based upon: at least one consecutive difference value related to the measured air flow rate is below the acceptable range of the third target value.

In accordance with one or more embodiments, the detection system may further include a third temperature sensor configured to detect a temperature of ambient air. According to at least one embodiment, the controller may be configured to measure a third series of temperatures with the third temperature sensor to produce a third time series of third measured temperature values. In various embodiments, the controller may be configured to create a first target value by calculating a predicted exhaust temperature. In some embodiments, the controller may be configured to create a second target value by calculating a predicted heat sink temperature.

According to one or more embodiments, the controller may be configured to calculate the predicted exhaust heat temperature and predicted heat sink temperature by using a prediction model. In various embodiments, the prediction model may be configured to generate the predicted exhaust heat temperature and predicted heat sink temperature based upon the time series of measured air flow rate values, the third time series of third measured temperature values, a system load value, and design parameters of the air-cooled system.

BRIEF DESCRIPTION OF THE FIGURES

The accompanying figures are not intended to be drawn to scale. In the figures, each identical or nearly identical component that is illustrated in various figures is represented by a like numeral. For purposes of clarity, not every component may be labeled in every figure. In the figures.

DETAILED DESCRIPTION OF THE DISCLOSURE

For the purposes of illustration only, and not to limit the generality, the present disclosure will now be described in detail with reference to the accompanying figures. This disclosure is not limited in its application to the details of construction and the arrangement of components set forth in the following description or illustrated in the drawings. The principles set forth in this disclosure are capable of other embodiments and of being practiced or carried out in various ways. In addition, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Methods and systems for identifying faults in an air-cooled system are disclosed. In accordance with one or more embodiments, the air-cooled system may include a power module. In certain embodiments the power module may be a power inverter or power converter. The term "power module," as used herein, generally refers to a unit that generates usable power, and, as a result, produces heat. However, the power module may include any heat-generating device, such as a power element, a control unit, or any other heat-producing electronic device which may be stored in a housing. The power module may include an inlet that functions to allow entry of airflow and an exhaust that functions to allow heat and airflow to exit the module. The air-cooled system may further include a heat sink that is secured to the power module to remove heat from the power module. The term "heat sink," as used herein, generally refers to a device or structure that has a principal purpose of dissipating or otherwise transferring heat from the heat-generating device of the power module. In certain instances the heat sink may be a structure that provides substantially high internal thermal conductivity and a surface area suitable for transferring heat to or from a surrounding medium (e.g., air, mixtures of gases other than air, pure gases, fluids, etc.). For example, in certain embodiments, the heat sink may include radiation fins.

The air-cooled system may further include an air-cooling device that is configured to deliver cooled air to the power module. For example, the air-cooling device may deliver cooled air to the heat sink of the power module. As used herein, the term "air-cooling device" refers to a structure or apparatus that is capable of transferring or delivering heat using a flow of air. In certain instances, the air-cooling device may be a fan or any device for removing air. The air-cooling device functions to dissipate or transfer heat out of or away from the power module, so as to reduce the temperature of the module.

In certain embodiments, the air-cooled system may include exhaust heat. The heat-generating component of the power module may produce heat that is transferred or absorbed by the heat sink and/or cooling air that is generated by the air-cooling device and flows through and around the interior of the power module. The heat that is dissipated or transferred to the flowing air may be discharged from the power module in the form of exhaust heat.

The air-cooled system may further include one or more sensors that are configured to detect one or more properties or characteristics of the air-cooled system. For example, the sensor may include a pressure, temperature, RF, or any other type of sensor known in the art. The sensors may also be configured to generate a signal representative of the property or characteristic of the air-cooled system. For example, the air-cooling device may include a sensor that detects fan speed, and the heat sink and exhaust heat may be equipped with one or more sensors that detect temperature. A temperature sensor may also be included in the air-cooled system that is configured to detect ambient temperature. The term "ambient temperature" generally refers to the temperature of air being supplied to the air-cooling device. In certain instances, the ambient temperature may be the temperature of an environment surrounding the power module. For example, if the power module is placed in a room, the ambient temperature may be the temperature of the room.

Figure 1:
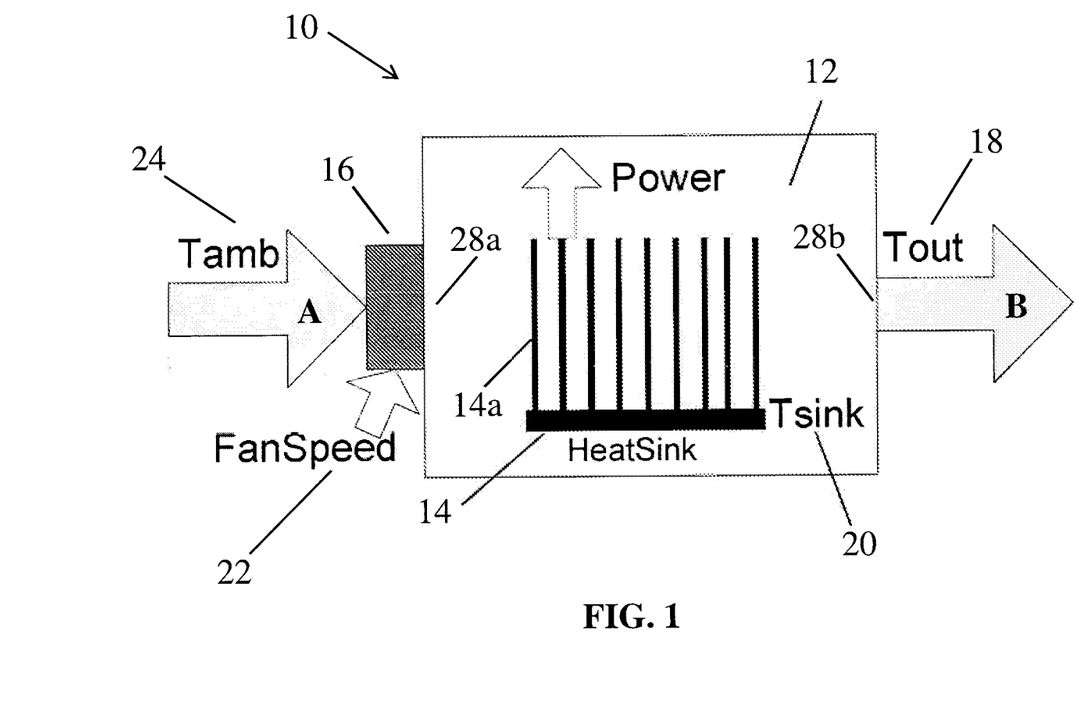
FIG. 1 is a schematic drawing of an air-cooled system in accordance with one or more aspects of the disclosure.

Referring to the drawings, and more particularly to FIG. 1, there is generally indicated at 10 an air-cooled system. The system 10 includes a power module 12, a heat sink 14 constructed with fins 14a, and an air-cooling device 16, such as a fan. In one embodiment, the heat sink 14 may be secured to the heat-generating component of the power module or otherwise configured to dissipate heat from the power module. The air-cooling device 16 may be placed near or at an inlet opening 28a in the power module 12. Heat produced by the power module 12 may be transferred to the heat sink 14, and exhausted through a discharge opening 28b formed in the power module 12. Airflow generated by the air-cooling device 16, which is indicated by arrows A and B, travels from the inlet opening 28a to the discharge opening 28b over the heat sink 14. This airflow contributes toward cooling down heat-producing components of the power module 12 by absorbing heat from the fins 14a of the heat sink 14.

The system 10 includes a sensor 18 configured to detect a temperature of the exhaust heat. The sensor 18 may be positioned at or near the discharge opening 28b. Another sensor 20 may be included to detect a temperature of the heat sink 14. The heat sink sensor 20 may be mounted on or positioned near the heat sink 14 of the power module 12. An air flow sensor 22 may be included that is configured to detect a rate of air flow through air-cooling device 16. In certain instances, the air flow sensor 22 may be a software implementation that is configured to detect a fan speed. In other instances, the air flow sensor 22 may be a tachometer positioned in the air-cooling device 16. The system 10 may further include a temperature sensor 24 configured to detect the ambient temperature. In some embodiments, the ambient temperature sensor 24 may be positioned external to the power module 12, for example, in locations where a room temperature is relatively uniform. In other embodiments, the ambient temperature sensor 24 may be located at or near the inlet opening 28a.

In certain instances, one or more faults related to components of the air-cooled system may occur. For example, the system may include one or more air filters that may become clogged or otherwise nonfunctional. The clogged air filter will subsequently restrict the flow of air through the system, thereby causing the temperature sensors placed at the heat sink and the exhaust heat to detect a subsequent increase in heat. The clogging of the air filter may be a slowly occurring event, meaning that the temperatures detected at the heat sink and exhaust heat may increase slowly. The amount of time it takes for the air filter to clog to a degree that triggers a fault may depend on the environment where the air-cooled system is located. For example, in a clean environment, such as a computer room, the clogging of the air filter may take many months or even a year. For dirtier environments, such as industrial settings, the air filter may clog on a much more regular basis, such as once or twice a month. In certain embodiments, the clogged air filter may cause the temperature sensor placed at the heat sink to detect an increase in temperature. For example, the temperature of the heat sink may increase from its steady-state temperature by about 10° C. The increase in temperature of the exhaust heat may be dependent upon the rate that air is flowing through the module or system.

In various embodiments, the one or more detected faults may be based on an air-cooled system that is operating under steady-state conditions. This means that the operating conditions under which all of the characterizing parameters affecting the heat output of the system, such as the fan speed, heat sink temperature, and exhaust heat temperature, change at a negligible rate. In other embodiments, the one or more detected faults may be based on dynamic conditions, meaning that one or more of the characterizing parameters change at a rapid rate.

Another type of fault that may occur includes a heat sink that has become clogged or is otherwise functioning improperly. Air may freely flow through the power module but the heat transfer from the heat sink to the air is decreased. The clogged heat sink will cause the sensor associated with the heat sink to detect an increase in heat. With this type of fault, the temperature sensor associated with the exhaust heat may not experience any significant changes, and may remain constant. This type of fault may also be a slowly occurring fault. Depending on the system environment and components, the heat sink may clog and need to be serviced (this may occur once a year or once every several years). The heat sink may clog due to other inoperable components in the system. For example, in systems that are designed with air filters, if one or more of the air filters are missing or inoperable for any other reason, then the heat sink may clog. Corrective action may include changing or replacing the air filters. In certain instances, this may occur within a short period of time, for example, within one month. In certain instances, the temperature of the heat sink may increase from its steady-state temperature by about 10° C.

An additional type of fault includes an issue with the consistency of air flow through the power module. For example, an object may block the air-cooling device, or the air-cooling device may malfunction. This type of fault may also occur when an air-cooled system is first started up in locations where there is an inadequate supply of air or in instances where the power module is installed incorrectly. For example, a power module that is not designed for mounting on a wall may exhibit this type of error if the power module is in fact installed on a wall. A problem with the air flow through the module may cause the temperature inside the module to increase. The air flow sensor associated with the air-cooling device may detect a decrease in air flow and the temperature sensors associated with the heat sink and the exhaust heat may detect an increase in heat. The problems associated with air flow may occur quickly, meaning that the temperatures detected at the heat sink and exhaust heat may increase rapidly, and the rate of air flow detected at the air-cooling device may decrease rapidly. In certain embodiments, it may be possible for a problem with air flow to be detected only from the sensor associated with the air-cooling device, meaning that a decrease in air flow is detected before the sensors associated with the heat sink and exhaust heat detect any increase in heat.

In accordance with one or more embodiments, a method is provided for identifying faults in an air-cooled system. The air-cooled system may include a first temperature sensor configured to detect a temperature of an exhaust heat, a second temperature sensor configured to detect a temperature of a heat sink, and an air flow sensor configured to detect a rate of air flow through an air-cooling device. The method may include measuring a first series of temperatures with the first temperature sensor to produce a first time series of first measured temperature values.

The time series of measured values may include two or more measurements taken over a time interval. The time interval may be any interval that is suitable for identifying a fault in the air-cooled system. For example, the time interval may be a fraction of a second. In certain embodiments, the time interval may be $1/1000$ of a second. In other embodiments, the time interval may be $1/100$ of a second.

The method may further include measuring a second series of temperatures with the second temperature sensor to produce a second time series of second measured temperature values. The method may further include measuring a series of rates of air flow with the air flow sensor to produce a time series of measured air flow rate values.

The method may further include identifying a fault in response to at least one of: (a) the first time series of the first measured temperature values being outside an acceptable range of a first target value; (b) the second time series of the second measured temperature values being outside an acceptable range of a second target value; and (c) the time series of the measured air flow rate values being outside an acceptable range of a third target value.

In at least one aspect, identifying the fault includes calculating a difference between consecutive measured values in the first time series to produce a first series of consecutive difference values related to the first measured temperature. In another aspect, identifying the fault includes calculating a difference between consecutive measured values in the second time series to produce a second series of consecutive difference values related to the second measured temperature. In a further aspect, identifying the fault includes calculating a difference between consecutive measured values in the time series of the measured air flow rate to produce a series of consecutive difference values related to the measured air flow rate.

In certain aspects, the method may further include determining a first type of fault based upon: the first series of consecutive difference values related to the first measured temperature are above the acceptable range of the first target value, the second series of consecutive difference values related to the second measured temperature are above the acceptable range of the second target value, and the series of consecutive difference values related to the measured air flow rate are within the acceptable range of the third target value. For example, the first type of fault may occur when an air filter is clogged. The temperatures associated with the exhaust heat and the heat sink may increase over time. According to this example, consecutive difference values corresponding to the exhaust heat and heat sink temperatures would increase, since each individual temperature measurement taken at each respective location would be increasing over time. When the target value is set at a value of zero (meaning a desire to have no increase in temperature), then the fault would be triggered, since the consecutive difference values would be above zero. At the same time, the consecutive difference values related to the measured air flow rate are not changing, and would fall within an acceptable target value set at zero.

In another aspect, the method may further include determining a second type of fault based upon: the first series of consecutive difference values related to the first measured temperature are within the acceptable range of the first target value, the second series of consecutive difference values related to the second measured temperature are above the acceptable range of the second target value; and the series of consecutive difference values related to the measured air flow rate are within the acceptable range of the third target value. The second type of fault may occur when a heat sink is clogged. The temperature associated with the heat sink may increase over time, while the temperature associated with the exhaust heat and the rate of air flow may remain constant. According to this example, consecutive difference values corresponding to the heat sink temperatures would increase, since each individual temperature measurement taken at the heat sink would be increasing over time. When the target value is set at a value of zero (meaning a desire to have no increase in temperature), then the fault would be triggered, since the consecutive difference values would be above zero. At the same time, the consecutive difference values related to the exhaust heat and measured air flow rate are not changing, and would fall within acceptable target values set at zero.

In at least one aspect, the method may further include determining a third type of fault based upon: the first series of consecutive difference values related to the first measured temperature are above the acceptable range of the first target value; the second series of consecutive difference values related to the second measured temperature are above the acceptable range of the second target value; and the series of consecutive difference values related to the measured air flow rate are below the acceptable range of the third target value. For example, the third type of fault may occur when an error associated with air flow occurs. The temperatures associated with the exhaust heat and the heat sink may increase rapidly over time, and the rate of air flow may decrease rapidly. According to this example, consecutive difference values corresponding to the exhaust heat temperature and the heat sink temperature would increase, and the air flow rate would decrease. When the respective target values are set at a value of zero, then the fault would be triggered.

In yet another aspect, the method may further include determining a fourth type of fault based upon: at least one consecutive difference value related to the measured air flow rate is below the acceptable range of the third target value. Like the third type of fault, this fault may occur when there is a problem with the air flow. However, the temperatures associated with the exhaust heat and the heat sink may not be affected, while the rate of air flow may decrease rapidly.

In at least one aspect, the method may further include determining a type of fault based upon: the first time series of the first measured temperature are above the acceptable range of the first target value, the second time series of the second measured temperature are above the acceptable range of the second target value, and the time series of the measured air flow rate are within the acceptable range of the third target value. For example, this type of fault may occur when an air filter is clogged. According to this example, consecutive measurements corresponding to the exhaust heat and heat sink temperatures would increase, since each individual temperature measurement taken at each respective location would be increasing over time. The target values may be determined by a prediction model (discussed below), and when the measured values for the exhaust heat and heat sink are higher than the corresponding target values, than the fault may be triggered.

In another aspect, the method may further include determining a type of fault based upon: the first time series of the first measured temperature are within the acceptable range of the first target value, the second time series of the second measured temperature are above the acceptable range of the second target value; and the time series of the measured air flow rate are within the acceptable range of the third target value. This type of fault may occur when a heat sink is clogged. According to this example, consecutive measurements corresponding to the heat sink temperatures would increase, since each individual temperature measurement taken at the heat sink would be increasing over time. The target value may be determined by a prediction model (discussed below), and when the measured values for the heat sink are higher than this target value, then the fault may be triggered.

In a further aspect, the method may further include determining a type of fault based upon: the first time series of the first measured temperature are above the acceptable range of the first target value; the second time series of the second measured temperature are above the acceptable range of the second target value; and the time series of measurements related to the air flow rate are below the acceptable range of the third target value. For instance, this type of fault may occur when an error associated with air flow occurs. According to this example, consecutive measurements corresponding to the exhaust heat temperature and the heat sink temperature would increase (and thus be higher than the respective predicted target values (discussed below)), and the air flow rate would decrease (and thus be lower than the predicted target value), then the fault would be triggered.

In yet another aspect, the method may further include determining yet another type of fault based upon: the time series of measurements related to the air flow rate are below the acceptable range of the third target value. This type fault may occur when there is a problem with the air flow.

In certain aspects, the air-cooled system may further include a third temperature sensor configured to detect a temperature of ambient air. The method may further include measuring a third series of temperatures with the third temperature sensor to produce a third time series of third measured temperature values.

In at least one embodiment, the first target value is created by calculating a predicted exhaust heat temperature and the second target value is created by calculating a predicted heat sink temperature. The predicted exhaust heat temperature and predicted heat sink temperature may be calculated by using a prediction model. The prediction model may be configured to generate the predicted exhaust heat temperature and predicted heat sink temperature based upon the time series of measured air flow rate values, the third time series of third measured temperature values related to ambient air, a system load value, and one or more design parameters of the air-cooled system. The one or more design parameters may represent, for example, the system efficiency and the transfer rate of the heat sink. The system efficiency and the transfer rate of the heat sink may be known based upon a given system design. For example, in some embodiments, the system may include an output converter with an efficiency of 99% and an input converter with an efficiency of 98.5%. In certain embodiments where the heat sink is operating under steady-state conditions, the heat transfer rate may be 100%. For example, when the heat sink temperature is stable, the heat sink transfer rate may be 100%. In certain instances, under steady-state conditions the heat sink temperature may be predicted based on the rate of air flow and the amount of energy added to the heat sink.

Figure 2:
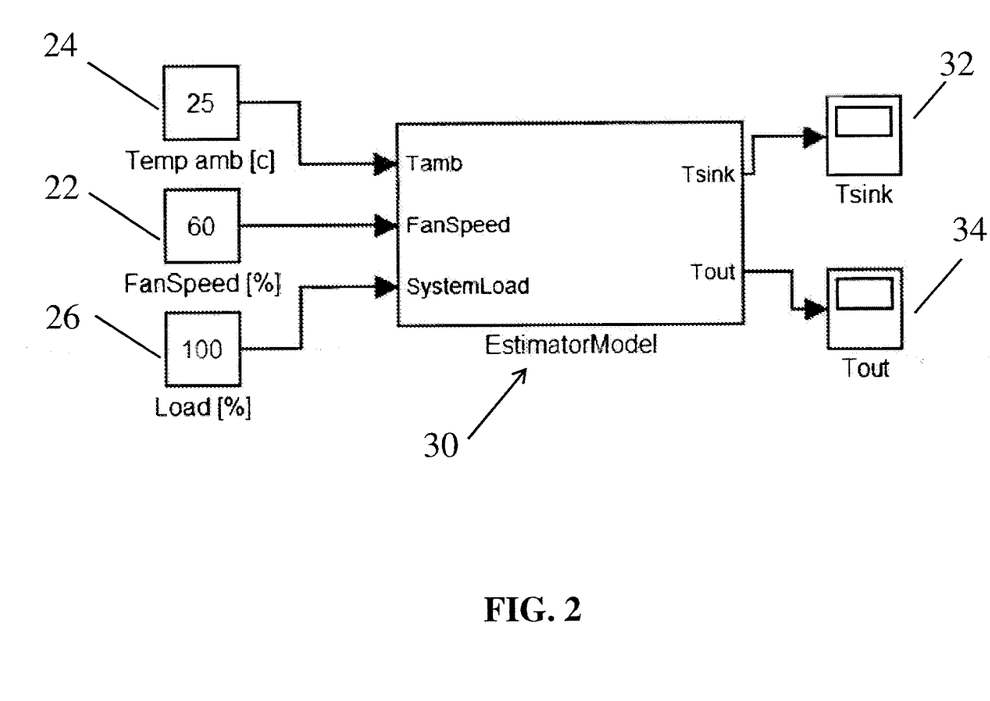
FIG. 2 is a schematic drawing of a prediction model in accordance with one or more aspects of the disclosure.

FIG. 2 is a schematic drawing of a prediction model generally indicated at 30 that may be used in identifying the cause of a fault in an air-cooled system. In general terms, one or more faults may be identified by making a comparison between sensor data taken from the air-cooled system and predicted data produced by the prediction model 30. The prediction model 30 calculates the predicted data based upon knowledge of the given system (e.g., system losses based upon various system loads and cooling abilities), the actual system load, ambient temperature, and the rate of air flow through the power module. Sensor data is taken from the ambient temperature sensor 24 and the air flow sensor 22. In addition, a given value for a system load 26 is also utilized by the prediction model 30. The system load 26 may refer to an actual system load. In a simple power module, the input load is equal to the output load. In one or more embodiments, the system load may be from 0-100%. In power modules where a single input converter is used for several output converters, or several input converters are used for a single output converter, the load on each converter must be individually calculated. The prediction model 30 is capable of calculating a predicted heat sink temperature 32 and a predicted exhaust heat temperature 34 based upon an energy balance between heat generated by the power module and heat that is absorbed by air flowing through the module. The thermal energy equation may be expressed by the relationship according to the equation: $Q=cm\Delta T$. This equation exemplifies the association between energy and temperature and states that energy (Q) is equal to a multiplication of the coefficient of specific heat (c), the object mass (m), and the temperature difference ($\Delta T$).

Based on the thermal energy equation discussed above, the heat sink temperature may be calculated according to the following equation: $\Delta T_{sink}=T(Q/(cm))$. Q is the amount of heat transferred to the heat sink and may be calculated based upon the input data for the system load and the system efficiency. For example, according to some embodiments, the system may include a converter with a load of 10 KW and an efficiency of 99%. In this system, the 100 W transferred to the heat sink indicates an energy transfer rate of 100 Joules per second to the heat sink. If there was no cooling effect, then the temperature of the heat sink would continue to increase based on the energy relationship: $Q=cm\Delta T$.

During the start-up phase, the heat sink temperature is equal to the ambient temperature ($T_{amb}$) which is known from the input sensor data, c is the coefficient of specific heat for the heat sink based upon the material used (e.g., aluminum), and m is the mass of the heat sink.

The energy balance of the system that includes the thermal energy equation may also be used to calculate the exhaust heat temperature ($T_{out}$). This is expressed by the equation $T_{out}=T_{amb}+(Q/cm))$. Q is the amount of energy transferred from the heat sink to the air flowing through the module, and may be calculated based upon the input data for the transfer rate of the heat sink, the rate of air flow, and the heat sink temperature. $T_{amb}$ is known from the input sensor data, c is the coefficient of specific heat for air, and m is the mass of air calculated from the rate of air flow. Under steady-state conditions, the amount of heat generated by the power module and transferred to the heat sink is equal to the amount of heat transferred from the heat sink to the air flowing through the module. The energy balance dictates that all the energy transferred from the converter to the heat sink is either stored in the heat sink as a thermal increase of the heat sink or is transferred to the flow of air as a thermal increase of the air. From known design specifications of the heat sink, the air flow, and the ambient temperature, the energy transfer to the flow of air may be calculated, and the thermal energy equation can be used to calculate the resulting air temperature. When calculating the heat sink temperature, the energy that was transferred from the heat sink to the flow of air must be accounted for, resulting in the actual heat sink temperature.

One or more various software programs known in the art may be used to calculate and implement the prediction model. For example, the prediction model may be programmed into MATLAB® (Mathworks, Inc., Natick, Mass.), with an exemplary result shown in FIG. 2. As shown, a system load 26 of 100%, a fan speed 22 of 60%, and an ambient temperature 24 of 25° C. may be introduced as input values to the prediction model 30. In various embodiments, such as in the given example, the fan speed may be represented by a value corresponding to capacity. In some embodiments, the fan speed may be represented by a digital number rating, for example, a rating ranging from a value of zero to 1024. Given these input values, the model yields a predicted heat sink temperature 32 of 55° C. and an exhaust temperature at 45° C. at a time interval of 200 seconds after applying a load step from 0-100%. These results may be compared and verified with results obtained from a lab that contains a known working power module. The prediction model of the power module depicted in FIG. 2 behaves in a linear manner, but in other embodiments the linear model may not be adequate to describe the complete range of operation. For these situations, several simple models or a more complex model may be implemented. The accuracy of the model may be determined by comparing the predicted values calculated by the prediction model against a working model in a lab environment.

Figure 3:
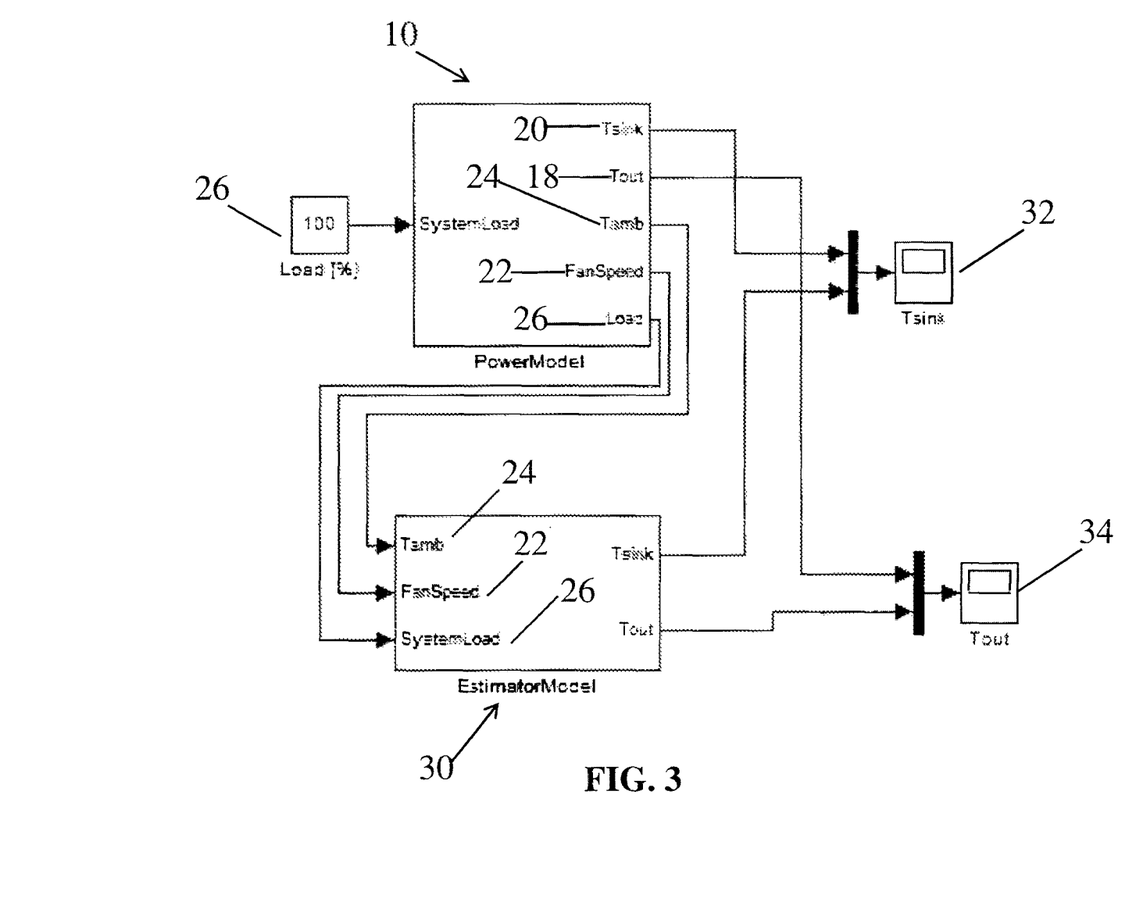
FIG. 3 is a schematic drawing of an air-cooled system in combination with a prediction model in accordance with one or more aspects of the disclosure.

The relationship between the prediction model 30 and the air-cooled system 10 is illustrated in FIG. 3. Input data supplied by the air-cooled system 10 that is included in the prediction model 30 includes the ambient temperature 24, the rate of air flow 22, and the system load 26. The prediction model uses these values to calculate a predicted heat sink temperature 32 and a predicted exhaust heat temperature 34, which are compared against the actual heat sink temperature 20 and exhaust heat temperature 18, respectively, as detected in the air-cooled system 10. When a fault is present, such as a clogged air filter, a difference in the temperatures measured in the power module and the predicted temperatures calculated in the prediction model will occur. This difference is caused by a change occurring in the dynamic heat transfer from the heat sink to the air caused by, for example, a reduction in the flow of air. The occurrence and behavior of this deviation identifies the presence and the type of fault that has occurred.

Figure 4:
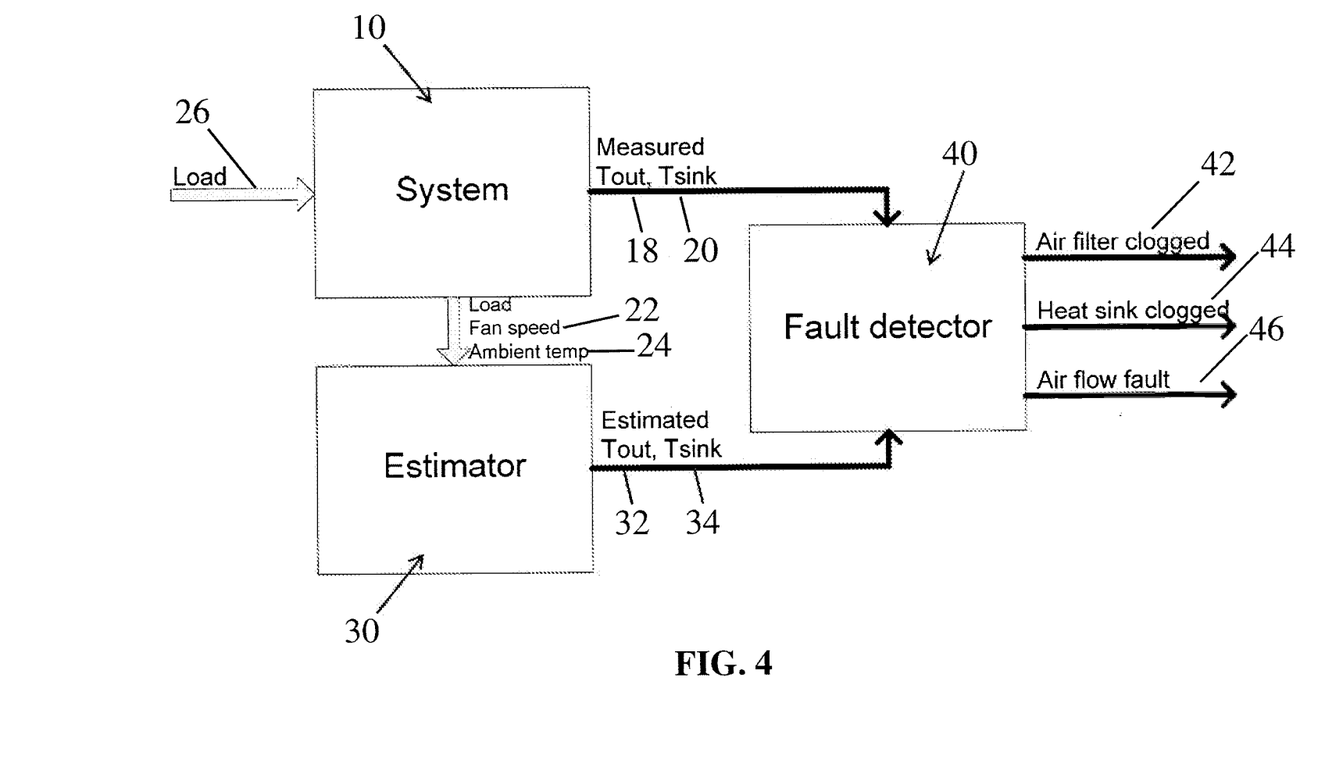
FIG. 4 is flow chart of an air-cooled system in combination with a prediction model in accordance with one or more aspects of the disclosure.

FIG. 4 illustrates a flow chart showing the air-cooled system 10 in combination with the prediction model 30 and a fault detection mechanism generally indicated at 40 that compares the measured system data against the predicted model data for both the heat sink temperature and the exhaust heat temperature. Based on these comparisons, the fault detection mechanism may produce one or more types of faults. For example, a fault 42 corresponding to a clogged air filter is represented by an increase in the exhaust heat temperature 18 and the heat sink temperature 20 detected in air-cooled system 10 when compared against the respective predicted values (32 and 34, respectively) generated by the prediction model 30. For this type of fault, the rate of air flow through the power module at a constant fan speed may be decreasing as the air filter becomes blocked over time. This may be a slow-occurring fault; meaning that the detected exhaust heat temperature 18 and heat sink temperature 20 may increase slowly over time. In the alternative, in certain air-cooled systems the fan speed may be increased automatically to compensate for a reduction in air flow. In this situation, the detected exhaust heat temperature 18 and heat sink temperature 20 will remain unchanged, but the predicted values (32 and 34, respectively) for these parameters will decrease.

In another example, a fault 44 corresponding to a clogged heat sink is represented by an increase in the heat sink temperature 20 when compared against the predicted heat sink temperature 34. When this type of fault occurs, air may be flowing freely through the power module, but the heat transfer from the sink to the air is decreased. This may also be a slowly occurring fault, meaning that the detected heat sink temperature 20 may increase slowly over time. The exhaust heat temperature may remain stable when this type of fault occurs.

A fault 46 corresponding to air flow is represented by an increase in the exhaust heat temperature 18 and heat sink temperature 20 when compared against the respective predicted values and additionally includes a corresponding decrease in the detected air flow rate 22. This type of fault may occur rapidly, meaning that the detected system parameters may increase (the temperature values) or decrease (the rate of air flow) rapidly over time. Fault 46 may also be represented by only a decrease in the detected air flow rate, without any corresponding increase in the detected heat sink 20 or exhaust heat 18 temperatures.

In certain instances, the prediction model may be based on steady-state conditions, meaning that deviations that occur between the measured system values and the predicted system values during a start-up or shut-down stage of a process may not be representative of one or more fault modes. It will be recognized by one of ordinary skill in the art that an actual active air-cooled system may have input parameters that vary over time. For example, the fan speed may be increased to compensate for a decrease in cooling that occurs due to a fault, such as a clogged air filter. The increase in fan speed may affect both the detected system parameters and predicted parameters produced by the prediction model. As a consequence, a deviation may not occur between these two sets of values.

In accordance with one or more embodiments, a detection system for identifying faults in an air-cooled system is provided. The detection system may be of the type used to cool air-cooled equipment having a heat sink. The air-cooled equipment may be a power module, as previously discussed. The detection system may include an air-cooling device configured to direct air over the heat sink. For instance, cooling air generated by the air-cooling device may flow over and around the heat sink and absorb and transfer heat away from the heat sink. The detection system may further include a temperature sensor configured to detect a temperature of an exhaust heat associated with the air-cooled equipment. Heat transferred to the air flowing through the air-cooled equipment may be subsequently discharged from the air-cooled equipment in the form of exhaust heat. A sensor may be placed at or near the discharge location to detect the temperature of the exhaust heat.

In one or more embodiments, the detection system may include a controller. As used herein, the term "controller" is meant to include one or more controllers that may be associated with one or more components of the detection system and that may cooperate in controlling various functions and operations of the system. The controller may be implemented in hardware, software, firmware, or some combination thereof. For example, the controller may include a single microprocessor or multiple microprocessors. The functionality associated with any controller may be centralized or distributed, whether locally or remotely. The controller may be in communication or otherwise be connected to one or more sensors placed in the system. For example, the controller may be in communication with one or more sensors associated with the exhaust heat, the heat sink, the air-cooling device, and the ambient air. The controller may be configured to measure one or more of a series of temperatures or other properties associated with these sensors. The controller may be configured to receive and interpret a signal from the one or more sensors. The controller may be configured to identify a fault in response to one or more of these series of measurements. For example, the controller may be configured to identify a fault in response to at least one of: (a) the time series of temperature measurements relating to the exhaust heat being outside an acceptable range of a first target value; (b) the time series of temperature measurements relating to the heat sink being outside an acceptable range of a second target value; and (c) the time series of the measured air flow rate value being outside an acceptable range of a third target value. The controller may also be configured to accommodate and apply the different functions of the prediction model, as previously discussed. For example, the controller may be configured to calculate the predicted exhaust heat and predicted heat sink values.

In certain instances, the controller may adjust one or more components of the air-cooled system in response to signals received from the sensors. For example, the fan speed may be adjusted (increased) in response to a detected increase in temperature in the heat sink or exhaust heat. These types of adjustments may occur before one or more faults, as previously discussed, are triggered.

At least one advantage of the disclosed systems and methods may include detecting a fault before a power module has to be powered down or taken offline. Further, when a problem is detected, the primary cause may be identified. An appropriate level of response may be assigned based on the severity of the problem. For example, an alarm may be activated or a field service technician may be notified when a certain type of fault occurs. In addition, a field service technician may be able to quickly resolve any problems based on the primary cause of the fault and act accordingly.

The systems and methods disclosed here may be embodied in the form of computer or controller implemented processes and apparatuses for practicing those processes. The present invention may also be embodied in the form of computer program code containing instructions embodied in tangible media, such as discs, CD-ROMs, hard drives, or any other computer-readable storage medium, wherein, when the computer program code is loaded into and executed by a computer/controller, the computer becomes an apparatus for practicing the invention.

Those skilled in the art will readily appreciate that the various parameters and configurations described herein are meant to be exemplary and that actual parameters and configurations will depend upon the specific application for which the embodiments directed toward the air flow fault detection methods and system of the present disclosure are used. Those skilled in the art will recognize, or be able to ascertain using no more than routine experimentation, many equivalents to the specific embodiments described herein. For example, those skilled in the art may recognize that embodiments according to the present disclosure may further include a plurality or network of power modules or may include a component of a production process using the power modules. It is, therefore, to be understood that the foregoing embodiments are presented by way of example only and that, within the scope of the appended claims and equivalents thereto, the disclosed air flow fault detection methods and systems may be practiced otherwise than as specifically described. The present systems and methods are directed to each individual feature or method described herein. In addition, any combination of two or more such features, apparatus or methods, if such features, apparatus or methods are not mutually inconsistent, is included within the scope of the present disclosure.

Further, it is to be appreciated various alterations, modifications, and improvements will readily occur to those skilled in the art. Such alterations, modifications, and improvements are intended to be part of this disclosure, and are intended to be within the spirit and scope of the disclosure. For example, an existing process may be modified to utilize or incorporate any one or more aspects of the disclosure. Thus, in some embodiments, embodiments may involve connecting or configuring an existing process to comprise the air flow fault detection methods and systems. For example, an existing air-cooling process may be retrofitted to involve use of a fault detection method in accordance with one or more embodiments. Accordingly, the foregoing description and drawings are by way of example only. Further, the depictions in the drawings do not limit the disclosures to the particularly illustrated representations.

While exemplary embodiments have been disclosed, many modifications, additions, and deletions may be made therein without departing from the spirit and scope of the disclosure and its equivalents, as set forth in the following claims.

What is claimed is:

1. A method of identifying faults in an air-cooled system, the air-cooled system including a first temperature sensor configured to detect a temperature of an exhaust heat, a second temperature sensor configured to detect a temperature of a heat sink secured to a heat-generating component, the heat sink having fins, each with a surface area configured to transfer heat to or from air surrounding the heat sink, and an air flow sensor configured to detect a rate of air flow through an air-cooling device, the method comprising:
   measuring a first series of temperatures with the first temperature sensor to produce a first time series of first measured temperature values;
   measuring a second series of temperatures with the second temperature sensor to produce a second time series of second measured temperature values;
   measuring a series of rates of air flow with the air flow sensor to produce a time series of measured air flow rate values; and
   identifying a fault in response to at least one of:
      the first time series of the first measured temperature values being outside an acceptable range of a first target value,
      the second time series of the second measured temperature values being outside an acceptable range of a second target value, and
      the time series of the measured air flow rate values being outside an acceptable range of a third target value.

2. The method of claim 1, wherein identifying the fault includes calculating a difference between consecutive measured values in the first time series to produce a first series of consecutive difference values related to the first measured temperature.

3. The method of claim 2, wherein identifying the fault includes calculating a difference between consecutive measured values in the second time series to produce a second series of consecutive difference values related to the second measured temperature.

4. The method of claim 3, wherein identifying the fault includes calculating a difference between consecutive measured values in the time series of the measured air flow rate to produce a series of consecutive difference values related to the measured air flow rate.

5. The method of claim 4, further comprising determining a first type of fault based upon:
   the first series of consecutive difference values related to the first measured temperature are above the acceptable range of the first target value,
   the second series of consecutive difference values related to the second measured temperature are above the acceptable range of the second target value, and
   the series of consecutive difference values related to the measured air flow rate are within the acceptable range of the third target value.

6. The method of claim 4, further comprising determining a second type of fault based upon:
   the first series of consecutive difference values related to the first measured temperature are within the acceptable range of the first target value,
   the second series of consecutive difference values related to the second measured temperature are above the acceptable range of the second target value, and
   the series of consecutive difference values related to the measured air flow rate are within the acceptable range of the third target value.

7. The method of claim 4, further comprising determining a third type of fault based upon:
   the first series of consecutive difference values related to the first measured temperature are above the acceptable range of the first target value,
   the second series of consecutive difference values related to the second measured temperature are above the acceptable range of the second target value, and
   the series of consecutive difference values related to the measured air flow rate are below the acceptable range of the third target value.

8. The method of claim 4, further comprising determining a fourth type of fault based upon:
   at least one consecutive difference value related to the measured air flow rate is below the acceptable range of the third target value.

9. The method of claim 1, wherein the air-cooled system further includes a third temperature sensor configured to detect a temperature of ambient air, the method further comprising measuring a third series of temperatures with the third temperature sensor to produce a third time series of third measured temperature values.

10. The method of claim 9, wherein the first target value is created by calculating a predicted exhaust heat temperature and the second target value is created by calculating a predicted heat sink temperature.

11. The method of claim 10, wherein the predicted exhaust heat temperature and predicted heat sink temperature are calculated by a prediction model, the prediction model configured to generate the predicted exhaust heat temperature and predicted heat sink temperature based upon the time series of measured air flow rate values, the third time series of third measured temperature values, a system load value, and design parameters of the air-cooled system.

12. The method of claim 11, wherein the prediction model is based upon an energy balance relationship according to the equation: Q=cmΔT.

13. A detection system for identifying faults in an air-cooled system of the type used to cool air-cooled equipment having a heat sink secured to a heat-generating component, the heat sink having fins, each with a surface area configured to transfer heat to or from air surrounding the heat sink, the detection system comprising:
   an air-cooling device configured to direct air over the heat sink;
   a first temperature sensor configured to detect a temperature of an exhaust heat associated with the air-cooled equipment;
   a second temperature sensor configured to detect a temperature of the heat sink;
   an air flow sensor configured to detect a rate of air flow through the air-cooling device; and
   a controller in communication with the first temperature sensor, the second temperature sensor, and the air flow sensor, the controller being configured to
      measure a first series of temperatures with the first temperature sensor to produce a first time series of first measured temperature values,
      measure a second series of temperatures with the second temperature sensor to produce a second time series of second measured temperature values,
      measure a series of rates of air flow with the air flow sensor to produce a time series of measured air flow rate values, and
      identify a fault in response to at least one of:
         the first time series of the first measured temperature values being outside an acceptable range of a first target value,
         the second time series of the second measured temperature values being outside an acceptable range of a second target value, and
         the time series of the measured air flow rate values being outside an acceptable range of a third target value.

14. The detection system of claim 13, wherein identifying the fault includes
   calculating a difference between consecutive measured values in the first time series to produce a first series of consecutive difference values related to the first measured temperature,
   calculating a difference between consecutive measured values in the second time series to produce a second series of consecutive difference values related to the second measured temperature, and
   calculating a difference between consecutive values in the time series of the measured air flow rate values to produce a series of consecutive difference values related to the measured air flow rate.

15. The detection system of claim 14, wherein the controller is configured to determine a first type of fault based upon:
   the first series of consecutive difference values related to the first measured temperature are above the acceptable range of the first target value,
   the second series of consecutive difference values related to the second measured temperature are above the acceptable range of the second target value, and
   the series of consecutive difference values related to the measured air flow rate are within the acceptable range of the third target value.

16. The detection system of claim 14, wherein the controller is configured to determine a second type of fault based upon:
   the first series of consecutive difference values related to the first measured temperature are within the acceptable range of the first target value,
   the second series of consecutive difference values related to the second measured temperature are above the acceptable range of the second target value, and
   the series of consecutive difference values related to the measured air flow rate are within the acceptable range of the third target value.

17. The detection system of claim 14, wherein the controller is configured to determine a third type of fault based upon:
   the first series of consecutive difference values related to the first measured temperature are above the acceptable range of the first target value,
   the second series of consecutive difference values related to the second measured temperature are above the acceptable range of the second target value, and
   the series of consecutive difference values related to the measured air flow rate are below the acceptable range of the third target value.

18. The detection system of claim 14, wherein the controller is configured to determine a fourth type of fault based upon:
   at least one consecutive difference value related to the measured air flow rate is below the acceptable range of the third target value.

19. The detection system of claim 13, further comprising a third temperature sensor configured to detect a temperature of ambient air, and
   wherein the controller is configured to
      measure a third series of temperatures with the third temperature sensor to produce a third time series of third measured temperature values, and
      the first target value is created by calculating a predicted exhaust temperature and the second target value is created by calculating a predicted heat sink temperature.

20. The detection system of claim 19, wherein the predicted exhaust heat temperature and predicted heat sink temperature are calculated by a prediction model, the prediction model configured to generate the predicted exhaust heat temperature and predicted heat sink temperature based upon the time series of measured air flow rate values, the third time series of third measured temperature values, a system load value, and design parameters of the air-cooled system.

* * * * *